United States Patent [19]

Oommen et al.

[11] Patent Number: 5,723,298

[45] Date of Patent: Mar. 3, 1998

[54] CYCLE LABELING AND SEQUENCING WITH THERMOSTABLE POLYMERASES

[75] Inventors: Abraham Oommen; Steve Roemer, both of Lincoln, Nebr.

[73] Assignee: Li-Cor, Inc., Lincoln, Nebr.

[21] Appl. No.: 714,562

[22] Filed: Sep. 16, 1996

[51] Int. Cl.⁶ .................. C12Q 1/68; C12P 19/34
[52] U.S. Cl. ........................... 435/6; 435/91.2
[58] Field of Search .............. 435/6, 91.2; 935/77, 935/78

[56] References Cited

U.S. PATENT DOCUMENTS 5,593,830   1/1997   Santamaria et al. .............. 435/6

OTHER PUBLICATIONS

Gyllensten *PCR–Technology* 1990, Henry A. Edrlich (editor), 1990.
Middendorf et al, Electrophoresis 13:487–494, 1992.
Lee, DNA & Cell Biol. 10(1):67–73, 1991.

*Primary Examiner*—Eggerton A. Campbell
*Attorney, Agent, or Firm*—Rothwell, Figg, Ernst & Kurz, PC

[57] ABSTRACT

The present invention provides a novel method for labeling and sequencing nucleic acid molecules, particularly DNA molecules in which an internally labeled, partially extended primer is elongated in a cycled primer extension reaction. An unlabeled DNA primer is contacted with a DNA template in the presence of suboptimal amounts of four dNTPs, one of which is labeled with a detectable marker which may be a fluorescent or visible fluorophor, and infared fluorophor or a radioactive label. This small, labeled primer extension product is then transferred to a new reaction where chain terminated primer extension products for DNA analysis are prepared.

20 Claims, No Drawings

CYCLE LABELING AND SEQUENCING WITH THERMOSTABLE POLYMERASES

The present invention relates to a novel method for labeling and sequencing nucleic acid molecules, particularly DNA molecules, which comprises preparing an internally labeled, partially extended, nucleic acid primer in a cycled primer extension reaction, and then utilizing this primer extension product in a cycled chain termination reaction to prepare samples that can be analyzed on a DNA sequencing gel, particularly by automated DNA sequencing.

BACKGROUND

Methods for sequencing nucleic acids rely on the detection of specific DNA molecules where these molecules have been labeled and resolved on DNA sequencing gels. Labels which have been used for DNA sequencing analysis include radioactive isotopes such as $^{32}P$ and $^{35}S$ and fluorescent dyes such as fluorescein. For sequencing methods that rely on primer extension reactions, the label can be incorporated into the DNA sequencing fragments by using primer molecules which have been previously labeled at their 5' ends, either by adding a label enzymatically, by incorporating the label during the chemical synthesis of the primer or by adding the label after primer synthesis, provided that primer was synthesized with adequate linkers. However, chemical synthesis of 5' fluorescent labeled oligonucleotide primers is in many instances time consuming and prohibitively expensive. Moreover, some fluorescent dyes may be adversely affected during primer synthesis. Therefore, there is still a need for reliable, inexpensive and efficient methods for labeling DNA molecules prior to their use in sequencing reactions, particularly when the DNA molecules need to be labeled with labels that are compatible with automated DNA sequences.

Procedures have been proposed for introducing labeled moieties into DNA molecules enzymatically, for example, by internally labeling the growing DNA chain with an a labeled dNTP (deoxynucleotide triphosphate). For example, G. De Bellis et al., (Biotechniques 19 (1995) pp. 66–70) have reported the labeling of DNA molecules with a fluorescent dye labeled dATP (deoxyadenosine) using T7 polymerase and only three of the four dNTPs normally found in DNA, in a limited chain elongation reaction. The specific dNTPs used are selected so that at least one fluorescence-labeled deoxynucleotide is incorporated, and into the extended primer the length of the extension product is limited by the absence of the 4th dNTP from the reaction. However, this technique requires that one know the sequence of the DNA immediately following the 3' end of the primer. In addition, because T7 polymerase is not a thermostable enzyme, this labeling reaction cannot be carried out as a cycled labeling reaction to prepare amplified quantities of labeled partially extended primers which can then be used to sequence DNA samples containing very small amounts of template.

Therefore, there is presently a need for improved methods for labeling DNA molecules for DNA sequence analysis, particularly where the amount of original template DNA is very limited. Linear amplification sequencing using thermostable DNA polymerase and random incorporation of fluorescent and dye labeled nucleotides could be used. However, such methods have not provided satisfactory results. Thus, there continues to be a need for less expensive, more reliable methods for preparing labeled nucleic acid molecules for sequencing, particularly for automated DNA sequencing.

DESCRIPTION OF THE INVENTION

The present invention provides a unique method for labeling DNA primers prior to DNA sequencing. This invention to a two-step process for sequencing a nucleic acid molecule which comprises first incorporating a labeled nucleoside into a DNA molecule to be sequenced by a controlled primer extension reaction. The labeled primer is then used in a second primer extension reaction containing chain terminating, dideoxy nucleotides to prepare samples which can be analyzed by automated DNA sequencing. The labeling reaction is a cycled reaction in which an unlabeled DNA primer is contacted with a DNA template in the presence of low or sub-optimal amounts of three unlabeled nucleotides of the possible 4 NTP's, dCTP, dGTP, dTTP and dATP, and the fourth being a labeled dNTP such that the primer can be partially extended for a few bases by a thermostable polymerase. Preferably, the primer is extended from one to 20 nucleotides. The temperature of the reaction mixture is cycled between a temperature which allows association or hybridization of the primer and the template DNA molecule, and subsequent extension of the primer by the DNA polymerase (a temperature which may be higher than the annealing temperature which is determined by the temperature for optimal activity of thermostable DNA polymerase used) and a temperature in which the new primer extension product and its template are denatured. Cooling the reaction mixture back to an optimal hybridization temperature results in the hybridization of new unlabeled primer molecule to template and the synthesis of additional primer extension products.

The second step of the method is a standard Linear Amplification Sequencing reaction which provides labeled DNA sequencing fragments for subsequent analysis, preferably by automated sequencing. The cycled chain termination reaction allows the preparation of sufficient quantities of sequencing reaction products to carry out sequencing on extremely small quantities of DNA.

Other features and advantages of the invention will be apparent from the following description of the examples and from the claims.

EXAMPLE

The labeling reaction is carried out by mixing the DNA template to be sequenced with a suitable primer, three unlabeled dNTPS and a fourth labeled dNTP, a suitable reaction buffer and a thermostable DNA polymerase in the quantities or concentrations indicated below.

| Labeling Reaction Mix | |
|---|---|
| 1. Combine the following in a 0.2 ml or 0.5 ml tube: | |
| a. DNA single stranded (0.1 to 0.3 pmol) double stranded (0.3 to 0.8 pmol) PCR products (0.1 to 0.3 pmol) | |
| b. Primer (2 pmol; up to 7 pmol) | — µl |
| C. dNTP Mix (5 µM dCTP, dGTP, dTTP) | 1.0 µl |
| d. IRD-40 dATP (20 pmol per µl) | 1.0 µl |
| e. 10X SequiTherm Reaction Buffer | 2.5 µl |
| f. SequiTherm DNA polymerase | 1.5 µl |
| g. Sterile, deionized water to total of 17 µl | — µl |

The DNA template may be either single-stranded, double-stranded or the product of a PCR reaction. The reaction components are mixed well and then overlaid with a drop of mineral oil to prevent evaporation. The tube is inserted into a thermal cycler which has been programed for an optimized cycled labeling reaction. A typical program for the Perkin Elmer Gene-Amp PCR System is (a) 92° C. for two minutes, (b) 92° for 30 seconds, (c) 50° C. for 20 seconds, and (d) 70° C. for 5 seconds. Steps b to d are repeated for a total of 40 cycles, after which the block is cooled to 4° C. Optimized programs for different thermocyclers can be determined by routine experimentation based on information provided by the machine's manufacturer. However, it is critical for the labeling that the correct annealing temperature is reached by the thermocycler used.

The reaction mixture indicated above is specific for the thermal stable enzyme Sequitherm DNA polymerase which may be obtained from Epicentre Technologies and infrared dye labeled dATP, IRD40 dATP, which may be obtained from Boehringer Mannheim Biochemicals (part number 1685635). Other thermostable polymerases may be used in the method of the present invention by substituting the reaction buffer recommended for the specific thermostable polymerase being used, provided that an adequate number of units of enzyme are added to the reaction mixture. The present inventors have successfully carried out the claimed method using the ThermoSequenase supplied by Amersham, Taq polymerase supplied by Boehringer Mannheim Biochemicals, the Circum Vent thermostable polymerase of New England Biolabs, and the Taq polymerase supplied by Promega in the fmol kit.

The sequencing reaction is carried out in four 0.2 ml PCR tubes which are labeled A, T, G and C. 2.0 µl of the appropriate chain termination reaction mixture, such as the Long Read™ LC termination mix from Epicentre Technologies is added to the appropriate tube. The termination mix contains appropriate amounts of dNTPS and the corresponding dideoxynucleotides. Four µl of the labeling reaction mixture from step 1 above is added to each termination tube. One of skill in the art will recognize that the concentrations should be adjusted to the optimum for the particular thermostable polymerase used. The contents of the tubes are mixed well, then overlaid with a drop of mineral oil. The tubes are carefully transferred to a thermal cycler and subjected to cycling temperatures of a cycle sequencing program which is optimized for the thermal cycler and primers being used. An optimized program for the Perkin-Elmer GeneAmp PCR Cycler is (a) 92° C. for 2 minutes, 92° C. for 30 seconds, (c) 50° C. for 15 seconds, and (d) 70° C. for 15 seconds. Steps b to d are repeated for a total of 30 cycles, then the block is cooled to 4° C. Optimized programs for different thermocyclers can be determined by routine experimentation based on information provided by the machine's manufacturer.

After the chain termination sequence reaction is completed, the reaction mix is pipetted from underneath the mineral oil and transferred to a fresh 0.5 ml tube. The reactions can be ethanol precipitated to remove excess label. To the dried DNA pellet obtained by ethanol precipitation is added 3.0 µl out of water and 2.0 µl of stop buffer. The samples are denatured by heating to 95° C. for two minutes, chilled on ice then loaded onto a standard sequencing gel.

Alternatively, the reaction mix can be immediately mixed with 4 µl of Stop buffer, heated to 98° C. to denature the nucleic acid in the sample and then directly loaded on to a DNA sequence gel.

EXAMPLE 2

PCR products can be labeled with a similar two step procedure. The labeling reaction will be very similar to that described above, but the extension reaction will be similar to a typical PCR. This way of labeling PCR products may be used with fluorophones attached to dNTPs and may be used in clinical, diagnostics and research applications that require PCR.

Random primer labeling of oligonucleotides is another situation where the two step procedure can be used to label DNA fragments. Again, this can also be accomplished in a cycling fashion with a thermostable DNA Polymerase.

While the present invention has been described and illustrated with details and references to certain embodiments, those of skill in the art will recognize that various modifications, changes, omissions and substitutions can be made without departing from the spirit of the invention.

We claim:

1. A method for labeling DNA for DNA sequence analysis comprising, preparing an internally labeled, partial nucleic acid primer extension product in a cycled primer extension reaction, wherein an unlabeled DNA primer is contacted with a DNA template in the presence of suboptimal amounts of four dNTPs, one of said dNTPs being a labeled dNTP, transferring the labeled partial primer extension product to a new reaction and preparing chain terminated primer extension products in a second cycled reaction.

2. The method of claim 1 wherein the primer extension product is labeled by incorporating a fluorescent fluorophor labeled dNTP.

3. The method of claim 2 wherein the primer extension product is labeled by incorporating a fluorescein labeled dNTP.

4. The method of claim 1 wherein the primer extension product is labeled by incorporating an infrared fluorophor labeled dNTP.

5. The method of claim 4 wherein the primer extension product is labeled by incorporating a dNTP labeled with IRD40.

6. The method of claim 1 wherein the primer extension product is labeled by incorporating a visible fluorophor labeled dNTP.

7. The method of claim 6 wherein the primer extension product is labeled by incorporating a dNTP labeled with a cyanine dye.

8. The method of claim 1 wherein the primer extension product is labeled by incorporating a radioactively labeled dNTP.

9. The method of claim 8 wherein the primer extension product is labeled by incorporating a radioactively labeled dNTP selected from the group consisting of alpha-$^{32}$P labeled dNTPs and alpha-$^{35}$S labeled dNTPs.

10. The method of claim 1 wherein the partial primer extension reaction contains from about 2 to 20 pmoles of dCTP, dGTP and dTTP and from about 2 to about 40 pmoles labeled dATP.

11. The method of claim 1 wherein the partially extended primer extension product is extended for about 1 to 100 bases.

12. The method of claim 1 wherein the partially extended primer extension product is extended for about 1 to 20 bases.

13. The method of claim 1 wherein the partially extended primer extension product is synthesized by a thermostable polymerase.

14. A method for labeling DNA samples for DNA sequence analysis comprising, preparing an internally labeled, partial nucleic acid primer extension product in a cycled primer extension reaction, wherein said reaction contains from about 2 to 20 pmoles of dCTP, dGTP and dTTP and from about 2 to 40 pmoles of labeled dATP, transferring the labeled partial primer extension product to a new reaction and preparing chain terminated primer extension products in a second cycled reaction.

15. A kit for preparing samples for nucleic acid sequence analysis comprising, an unlabeled nucleic acid primer, a labeled dNTP, three unlabeled dNTPs with the proviso that said unlabeled dNTPs are different from said labeled dNTP, a thermostable polymerase and a thermostable polymerase reaction buffer.

16. The kit of claim 14 wherein the thermostable polymerase is Sequitherm DNA polymerase.

17. The kit of claim 14 wherein the labeled dNTP is IRD-40 dATP and the unlabeled nucleotides are dCTP, dGTP and dTTP.

18. The kit of claim 14 wherein the labeled dNTP is a radioactively labeled dNTP.

19. The kit of claim 14 wherein the labeled dNTP is an infrared dye labeled dNTP.

20. The kit of claim 14 wherein the labeled dNTP is a visible dye labeled dNTP.

* * * * *